United States Patent
Shluzas et al.

[11] Patent Number: 6,146,406
[45] Date of Patent: Nov. 14, 2000

[54] BONE ANCHOR

[75] Inventors: Alan E. Shluzas, Millis; Steve Reynolds, Attleboro; William R. Davis, Hingham; Paul Brophy, Rayham, all of Mass.

[73] Assignee: Smith & Nephew, Inc., Memphis, Tenn.

[21] Appl. No.: 09/022,560

[22] Filed: Feb. 12, 1998

[51] Int. Cl.⁷ ................................................. A61B 17/04
[52] U.S. Cl. ............................. 606/232; 606/60; 606/62
[58] Field of Search .................................. 606/61, 62, 63, 606/64, 65, 232, 104, 233, 139, 140, 144, 148

[56] References Cited

U.S. PATENT DOCUMENTS

| | | |
|---|---|---|
| Re. 34,293 | 6/1993 | Goble et al. . |
| Re. 34,762 | 10/1994 | Goble et al. . |
| D. 331,626 | 12/1992 | Hayhurst et al. . |
| 1,247,621 | 1/1917 | Bennett . |
| 2,065,659 | 12/1936 | Cullen . |
| 2,100,570 | 11/1937 | Saleh et al. . |
| 2,143,086 | 1/1939 | Pleister . |
| 2,213,715 | 9/1940 | Costello . |
| 2,453,056 | 3/1948 | Zack . |
| 2,562,419 | 7/1951 | Ferris . |
| 2,665,597 | 1/1954 | Hill . |
| 2,669,774 | 1/1954 | Livingston . |
| 2,883,096 | 4/1959 | Dawson . |
| 3,003,155 | 10/1961 | Mielzynski et al. . |
| 3,048,177 | 8/1962 | Takaro . |
| 3,103,666 | 9/1963 | Bone . |

(List continued on next page.)

FOREIGN PATENT DOCUMENTS

| | | |
|---|---|---|
| 0 129 442 A1 | 6/1984 | European Pat. Off. . |
| 0 129 422 A1 | 12/1984 | European Pat. Off. . |
| 0129442 A1 | 12/1984 | European Pat. Off. ............... 606/144 |
| 0 270 704 A1 | 12/1986 | European Pat. Off. . |
| 0 241 240 A1 | 10/1987 | European Pat. Off. . |
| 0 340 159 A1 | 3/1989 | European Pat. Off. . |
| 0 409 364 A2 | 5/1990 | European Pat. Off. . |
| 0 502 509 A1 | 3/1992 | European Pat. Off. . |
| 0 574 707 A1 | 5/1993 | European Pat. Off. . |
| 0 591 991 A2 | 10/1993 | European Pat. Off. . |
| 0 674 880 A1 | 3/1995 | European Pat. Off. . |
| 1 368 021 | 9/1963 | France . |
| 2 622 430 | 10/1987 | France . |
| 0 615 732 A1 | 9/1991 | France . |
| 343992 | 3/1931 | United Kingdom . |
| 2118474 | 11/1983 | United Kingdom . |
| WO 86/03666 | 7/1986 | WIPO . |
| WO 87/01270 | 3/1987 | WIPO . |
| WO 89/10096 | 11/1989 | WIPO . |
| WO 92/04874 | 4/1992 | WIPO . |
| WO 95/00836 | 1/1995 | WIPO . |
| WO 95/25469 | 9/1995 | WIPO . |
| WO 95/29637 | 11/1995 | WIPO . |
| WO 95/32670 | 12/1995 | WIPO . |

OTHER PUBLICATIONS

Anchor System, Patented Anchor Design.
ID Innovasive Devices Inc., "Product Focus ROC Fastener System", 1994.

Primary Examiner—Michael Buiz
Assistant Examiner—Lien Ngo
Attorney, Agent, or Firm—Fish & Richardson P.C.

[57] ABSTRACT

A bone anchor includes first and second anchoring legs and a bridge joining the anchoring legs between their proximal and distal ends. Portions of the anchoring legs on a proximal side of the bridge are configured to elastically compress together in response to an insertion force applied to the bone anchor during insertion of the bone anchor into a bone hole, and to plastically splay apart in response to a withdrawal force applied to the bone anchor. Portions of the anchoring legs on a distal side of the bridge are configured to compress together in during application of the withdrawal force to limit the splaying of the proximal portions of the anchoring legs. A method for attaching soft tissue to bone includes inserting the bone anchor with attached suture into the bone, and deploying the bone anchor within the bone by applying tension to the suture.

36 Claims, 4 Drawing Sheets

6,146,406
Page 2

U.S. PATENT DOCUMENTS

| | | |
|---|---|---|
| 3,123,077 | 3/1964 | Alcamo . |
| 3,143,915 | 8/1964 | Tendler . |
| 3,155,095 | 11/1964 | Brown . |
| 3,227,031 | 1/1966 | Williams . |
| 3,254,650 | 6/1966 | Collito . |
| 3,316,796 | 5/1967 | Young . |
| 3,399,432 | 9/1968 | Merser . |
| 3,470,834 | 10/1969 | Bone . |
| 3,527,233 | 9/1970 | Matthews . |
| 3,541,591 | 11/1970 | Hoegerman . |
| 3,570,447 | 3/1971 | Basseches . |
| 3,664,345 | 5/1972 | Dabbs et al. . |
| 3,695,271 | 10/1972 | Chowdorow . |
| 3,699,969 | 10/1972 | Allen . |
| 3,716,058 | 2/1973 | Tanner, Jr. . |
| 3,845,772 | 11/1974 | Smith . |
| 3,875,648 | 4/1975 | Bone . |
| 3,910,281 | 10/1975 | Kletschka et al. . |
| 3,931,667 | 1/1976 | Mercer . |
| 3,976,079 | 8/1976 | Samuels et al. . |
| 3,990,619 | 11/1976 | Russell . |
| 4,006,747 | 2/1977 | Kronenthal et al. . |
| 4,011,602 | 3/1977 | Rybicki et al. . |
| 4,013,071 | 3/1977 | Rosenberg . |
| 4,185,636 | 1/1980 | Gobbax . |
| 4,233,981 | 11/1980 | Schomacher . |
| 4,235,238 | 11/1980 | Ogui et al. . |
| 4,275,490 | 6/1981 | Bivins . |
| 4,275,717 | 6/1981 | Bolesky . |
| 4,286,807 | 9/1981 | Bächli . |
| 4,287,807 | 9/1981 | Pacharis et al. . |
| 4,291,698 | 9/1981 | Fuchs et al. . |
| 4,293,259 | 10/1981 | Liebig . |
| 4,326,531 | 4/1982 | Shimonaka . |
| 4,379,451 | 4/1983 | Getscher . |
| 4,386,515 | 6/1983 | Starke . |
| 4,409,974 | 10/1983 | Freedland . |
| 4,414,967 | 11/1983 | Shapiro . |
| 4,447,915 | 5/1984 | Weber . |
| 4,454,612 | 6/1984 | McDaniel et al. . |
| 4,454,875 | 6/1984 | Pratt et al. . |
| 4,462,395 | 7/1984 | Johnson . |
| 4,469,101 | 9/1984 | Coleman et al. . |
| 4,493,323 | 1/1985 | Albright et al. . |
| 4,501,266 | 2/1985 | McDaniel . |
| 4,525,114 | 6/1985 | Hirst . |
| 4,532,926 | 8/1985 | O'Holla . |
| 4,573,844 | 3/1986 | Smith . |
| 4,590,928 | 5/1986 | Hunt et al. . |
| 4,602,635 | 7/1986 | Mulhollan et al. . |
| 4,621,640 | 11/1986 | Mulhollan et al. . |
| 4,632,100 | 12/1986 | Somers et al. . |
| 4,636,121 | 1/1987 | Miller . |
| 4,667,675 | 5/1987 | Davis . |
| 4,669,473 | 6/1987 | Richards et al. . |
| 4,708,132 | 11/1987 | Silvestrini . |
| 4,738,255 | 4/1988 | Goble et al. . |
| 4,741,330 | 5/1988 | Hayhurst . |
| 4,744,353 | 5/1988 | McFarland . |
| 4,744,793 | 5/1988 | Parr et al. . |
| 4,747,407 | 5/1988 | Liu et al. . |
| 4,750,492 | 6/1988 | Jacobs . |
| 4,759,765 | 7/1988 | Van Kampen . |
| 4,772,286 | 9/1988 | Goble et al. . |
| 4,776,328 | 10/1988 | Frey et al. . |
| 4,776,330 | 10/1988 | Chapman et al. . |
| 4,825,621 | 5/1989 | Jensen . |
| 4,870,957 | 10/1989 | Goble et al. . |
| 4,875,474 | 10/1989 | Border . |
| 4,892,547 | 1/1990 | Brown . |
| 4,898,156 | 2/1990 | Gatturna et al. . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. . |
| 4,946,468 | 8/1990 | Li . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble . |
| 4,986,263 | 1/1991 | Dickerson et al. . |
| 4,997,433 | 3/1991 | Goble et al. . |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1991 | Wiley . |
| 5,037,422 | 8/1991 | Hayhurst et al. . |
| 5,037,426 | 8/1991 | Goble et al. . |
| 5,041,129 | 8/1991 | Hayhurst et al. . |
| 5,046,513 | 9/1991 | Gatturna et al. . |
| 5,065,490 | 11/1991 | Wivagg et al. .......... 606/232 |
| 5,078,730 | 1/1992 | Li et al. . |
| 5,078,731 | 1/1992 | Hayhurst . |
| 5,084,058 | 1/1992 | Li . |
| 5,087,263 | 2/1992 | Li . |
| 5,092,891 | 3/1992 | Kummer et al. . |
| 5,094,563 | 3/1992 | Carletti . |
| 5,100,417 | 3/1992 | Cerier et al. . |
| 5,129,902 | 7/1992 | Goble et al. . |
| 5,133,723 | 7/1992 | Li et al. . |
| 5,141,520 | 8/1992 | Goble et al. . |
| 5,147,166 | 9/1992 | Harker . |
| 5,147,362 | 9/1992 | Goble . |
| 5,152,764 | 10/1992 | Goble . |
| 5,152,790 | 10/1992 | Rosenberg et al. . |
| 5,156,616 | 10/1992 | Meadows et al. ........ 606/232 |
| 5,161,916 | 11/1992 | White et al. . |
| 5,163,946 | 11/1992 | Li . |
| 5,167,665 | 12/1992 | McKinney . |
| 5,174,087 | 12/1992 | Bruno . |
| 5,176,682 | 1/1993 | Chow . |
| 5,192,303 | 3/1993 | Gatturna et al. . |
| 5,203,787 | 4/1993 | Noblitt et al. . |
| 5,207,679 | 5/1993 | Li . |
| 5,209,753 | 5/1993 | Biedermann et al. . |
| 5,211,647 | 5/1993 | Schmieding . |
| 5,217,486 | 6/1993 | Rice et al. . |
| 5,224,946 | 7/1993 | Hayhurst et al. . |
| 5,236,445 | 8/1993 | Hayhurst et al. . |
| 5,250,054 | 10/1993 | Li . |
| 5,250,058 | 10/1993 | Miller et al. . |
| 5,263,802 | 11/1993 | Fichot et al. . |
| 5,263,991 | 11/1993 | Wiley et al. . |
| 5,266,075 | 11/1993 | Clark et al. . |
| 5,268,001 | 12/1993 | Nicholson et al. . |
| 5,300,077 | 4/1994 | Howell . |
| 5,306,290 | 4/1994 | Martins et al. . |
| 5,312,416 | 5/1994 | Spaeth et al. . |
| 5,312,422 | 5/1994 | Trott . |
| 5,312,438 | 5/1994 | Johnson . |
| 5,313,962 | 5/1994 | Obenchain . |
| 5,314,427 | 5/1994 | Goble et al. . |
| 5,314,429 | 5/1994 | Goble . |
| 5,314,433 | 5/1994 | Li . |
| 5,318,577 | 6/1994 | Li . |
| 5,324,308 | 6/1994 | Pierce . |
| 5,326,205 | 7/1994 | Anspach, Jr. et al. . |
| 5,330,534 | 7/1994 | Herrington et al. . |
| 5,342,366 | 8/1994 | Whiteside et al. . |
| 5,350,380 | 9/1994 | Goble et al. . |
| 5,354,298 | 10/1994 | Lee et al. . |

| | | | | | |
|---|---|---|---|---|---|
| 5,354,299 | 10/1994 | Coleman . | 5,486,197 | 1/1996 | Le et al. . |
| 5,354,300 | 10/1994 | Goble et al. . | 5,500,001 | 3/1996 | Trott . |
| 5,356,413 | 10/1994 | Martins et al. . | 5,501,683 | 3/1996 | Trott . |
| 5,358,511 | 10/1994 | Gatturna et al. . | 5,501,695 | 3/1996 | Anspach, Jr. et al. . |
| 5,364,400 | 11/1994 | Rego, Jr. et al. . | 5,505,735 | 4/1996 | Li . |
| 5,370,662 | 12/1994 | Stone et al. ............... 606/232 | 5,507,812 | 4/1996 | Moore . |
| 5,372,599 | 12/1994 | Martins . | 5,520,691 | 5/1996 | Branch . |
| 5,372,604 | 12/1994 | Trott . | 5,520,696 | 5/1996 | Wenstrom, Jr. . |
| 5,376,120 | 12/1994 | Sarver et al. . | 5,522,844 | 6/1996 | Johnson ................. 606/232 |
| 5,383,878 | 1/1995 | Roger et al. . | 5,522,845 | 6/1996 | Wenstrom, Jr. . |
| 5,391,170 | 2/1995 | McGuire et al. . | 5,531,792 | 7/1996 | Huene . |
| 5,393,302 | 2/1995 | Clark et al. . | 5,534,004 | 7/1996 | Santangelo . |
| 5,397,356 | 3/1995 | Goble et al. . | 5,545,180 | 8/1996 | Le et al. . |
| 5,411,506 | 5/1995 | Goble et al. . | 5,549,636 | 8/1996 | Li . |
| 5,411,523 | 5/1995 | Goble . | 5,554,171 | 9/1996 | Gatturna et al. . |
| 5,417,712 | 5/1995 | Whitaker et al. . | 5,562,683 | 10/1996 | Chan . |
| 5,423,819 | 6/1995 | Small et al. . | 5,562,687 | 10/1996 | Chan . |
| 5,423,860 | 6/1995 | Lizardi et al. . | 5,571,104 | 11/1996 | Li . |
| 5,425,733 | 6/1995 | Schmieding . | 5,573,548 | 11/1996 | Nazre et al. . |
| 5,425,767 | 6/1995 | Steininger et al. . | 5,575,805 | 11/1996 | Li . |
| 5,431,651 | 7/1995 | Goble et al. . | 5,578,057 | 11/1996 | Wenstrom, Jr. . |
| 5,439,470 | 8/1995 | Li . | 5,584,835 | 12/1996 | Greenfield ............... 606/232 |
| 5,439,474 | 8/1995 | Li . | 5,584,860 | 12/1996 | Goble et al. . |
| 5,439,684 | 8/1995 | Prewett et al. . | 5,607,432 | 3/1997 | Fucci ..................... 606/104 |
| 5,441,502 | 8/1995 | Bartlett . | 5,643,266 | 7/1997 | Li . |
| 5,443,472 | 8/1995 | Li . | 5,643,321 | 7/1997 | McDevitt . |
| 5,443,482 | 8/1995 | Stone et al. . | 5,645,589 | 7/1997 | Li . |
| 5,443,509 | 8/1995 | Boucher et al. . | 5,647,874 | 7/1997 | Hayhurst ................. 606/232 |
| 5,449,366 | 9/1995 | Li . | 5,649,963 | 7/1997 | McDevitt . |
| 5,454,811 | 10/1995 | Huebner . | 5,662,654 | 9/1997 | Thompson . |
| 5,456,685 | 10/1995 | Li . | 5,683,418 | 11/1997 | Luscombe et al. . |
| 5,458,601 | 10/1995 | Young, Jr. et al. . | 5,690,649 | 11/1997 | Li . |
| 5,464,189 | 11/1995 | Li . | 5,697,950 | 12/1997 | Fucci et al. ............... 606/232 |
| 5,464,425 | 11/1995 | Skiba . | 5,707,394 | 1/1998 | Miller et al. ............. 606/232 |
| 5,464,427 | 11/1995 | Curtis et al. . | 5,707,395 | 1/1998 | Li . |
| 5,470,334 | 11/1995 | Ross et al. . | 5,741,300 | 4/1998 | Li ........................... 606/232 |
| 5,472,452 | 12/1995 | Trott ....................... 606/232 | 5,749,899 | 5/1998 | Bardin ..................... 606/232 |
| 5,480,403 | 1/1996 | Lee et al. . | | | |

BONE ANCHOR

CROSS REFERENCE TO RELATED APPLICATION

This application is related to copending U.S. application Ser. No. 09/022,746, filed Feb. 12, 1998, titled BONE ANCHOR DELIVERY SYSTEM, incorporated by reference herein.

BACKGROUND OF THE INVENTION

The invention relates to bone anchors.

Bone anchors are commonly used to attach soft tissue to bone, e.g., during rotator cuff ligament reconstruction. It is known to place an anchor having an attached suture into a bone hole. The suture can then be used to attach soft tissue to the bone.

SUMMARY OF THE INVENTION

According to one aspect of the invention, a bone anchor includes first and second anchoring legs and a bridge joining the anchoring legs between their proximal and distal ends.

Embodiments may include one or more of the following features. Portions of the anchoring legs on a proximal side of the bridge are configured to compress together in response to an insertion force applied to the bone anchor during insertion of the bone anchor into a bone hole, and to splay apart in response to a withdrawal force applied to the bone anchor when the bone anchor is located in the bone hole. The anchoring legs undergo elastic deformation when compressed together, and plastic deformation when splayed apart.

Portions of the anchoring legs on a distal side of the bridge are configured to compress together during application of the withdrawal force to limit the splaying of the proximal portions of the anchoring legs. The distal portions of the legs define a slot therebetween. A width of the slot defines an amount of splaying of the legs.

Preferably, the anchoring legs are oriented substantially parallel to each other along a longitudinal axis, and the bridge is positioned transverse to the anchoring legs. The bridge includes an axially oriented opening for placement of the bone anchor over a guidewire.

The bone anchor includes a suture mount for attaching suture to the bone anchor. The suture mount includes a transversely oriented through hole in at least one of the anchoring legs, and an axially oriented groove located on an outer surface of the bone anchor, adjacent to and on either side of the through hole. There is a transversely oriented through hole in the first anchoring leg and in the second anchoring leg.

The anchoring legs each includes a distal end configured for penetrating bone tissue. The anchoring legs include portions distal of the bridge which define a slot therebetween. Each leg includes an inner surface configured to engage a flattened region of an insertion tool. The legs have outwardly curved proximal ends.

According to another aspect of the invention, a bone anchor includes a plurality of anchoring legs each having a proximal end and a distal end. Proximal portions of the plurality of anchoring legs are configured to splay apart during application of a withdrawal force to the bone anchor when the bone anchor is located in a bone hole. Distal portions of the plurality of anchoring legs are configured to compress together during application of the withdrawal force to limit splaying of the proximal portions of the plurality of anchoring legs.

According to another aspect of the invention, a method for attaching soft tissue to bone includes inserting a bone anchor with attached suture into the bone. The bone anchor has a first anchoring leg, a second anchoring leg, and a bridge joining the anchoring legs between their proximal and distal ends. The bone anchor is deployed within the bone by applying tension to the suture.

Aspects of this embodiment of the invention may include deploying the bone anchor by pulling proximally on the suture to plastically splay apart proximal portions of the anchoring legs.

The bone anchor allows a plurality of sutures to be attached to the anchor, increasing the attachment area of soft tissue to bone. The placement of the bridge enables the distal portions of the anchoring legs to act to limit the deformation of the proximal portions of the anchoring legs. The bone anchor can be delivered over a previously placed guidewire facilitating placement of the anchor within a bone hole without visualization of the bone hole.

Other features and advantages of the invention will be apparent from the following detailed description, and from the claims.

DESCRIPTION OF PREFERRED EMBODIMENTS

Figure 1:
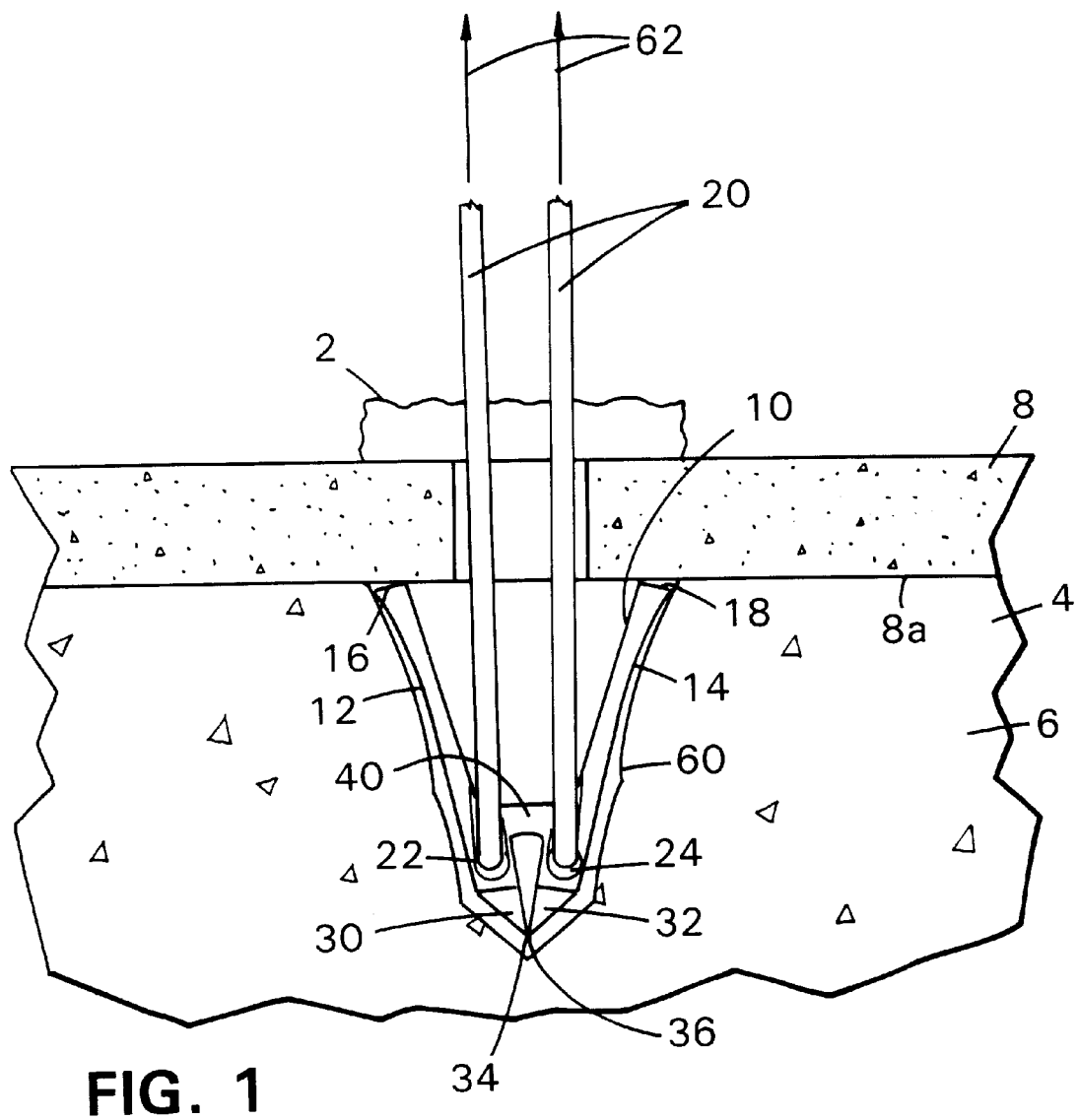
FIG. 1 illustrates a bone anchor according to the invention shown in a deployed state.

Referring to FIG. 1, a bone anchor, e.g., a suture anchor 10, for reattaching soft tissue 2 to bone 4 with suture, includes flexible anchoring legs 12, 14. Anchoring legs 12, 14 act to secure suture anchor 10 within cancellous bone 6 with proximal ends 16, 18 of legs 12, 14, respectively, abutting against the undersurface 8a of cortical bone 8. A pair of sutures 20 for tying soft tissue 2 to bone 4 are passed through transversely extending holes 22, 24 in legs 12, 14, respectively.

Figure 2A:
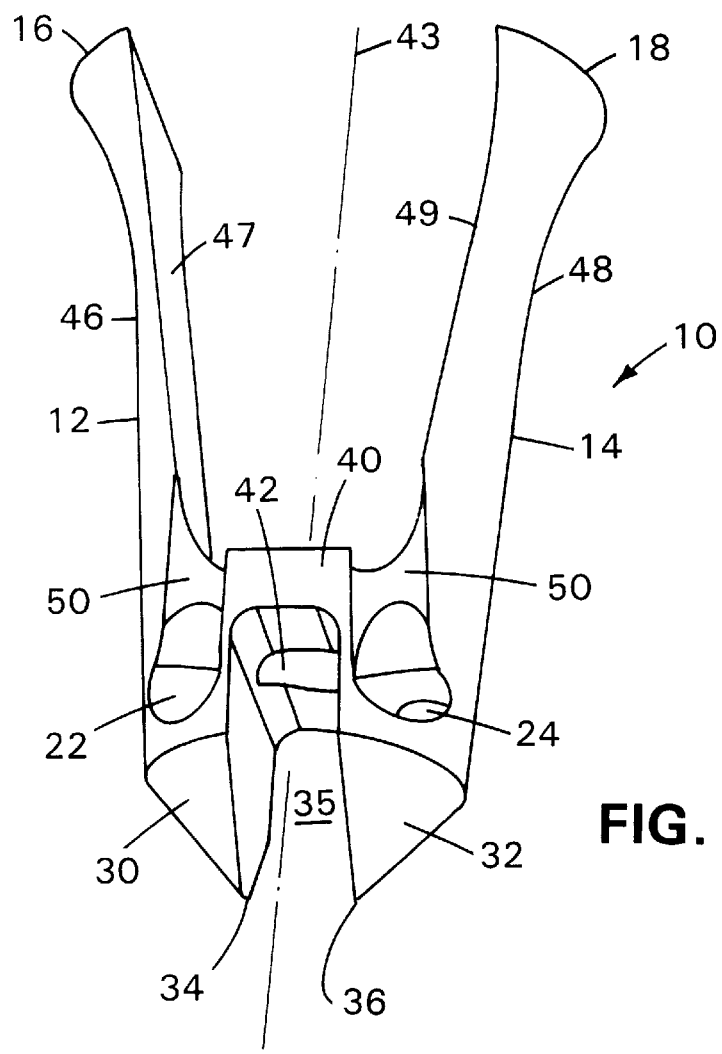
FIG. 2A is a perspective view of the bone anchor of FIG. 1 shown in an uncompressed state.
Figure 2B:
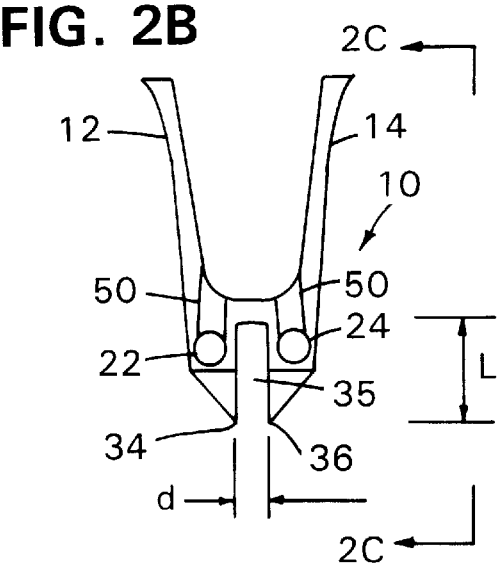
FIG. 2B is a side view of the bone anchor of FIG. 2A.
Figure 2C:
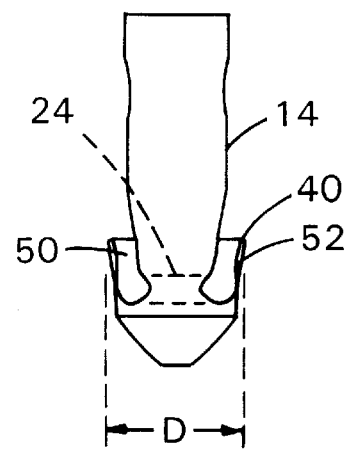
FIG. 2C is another side view of the bone anchor, taken along line 2C—2C of FIG. 2B.
Figure 3:
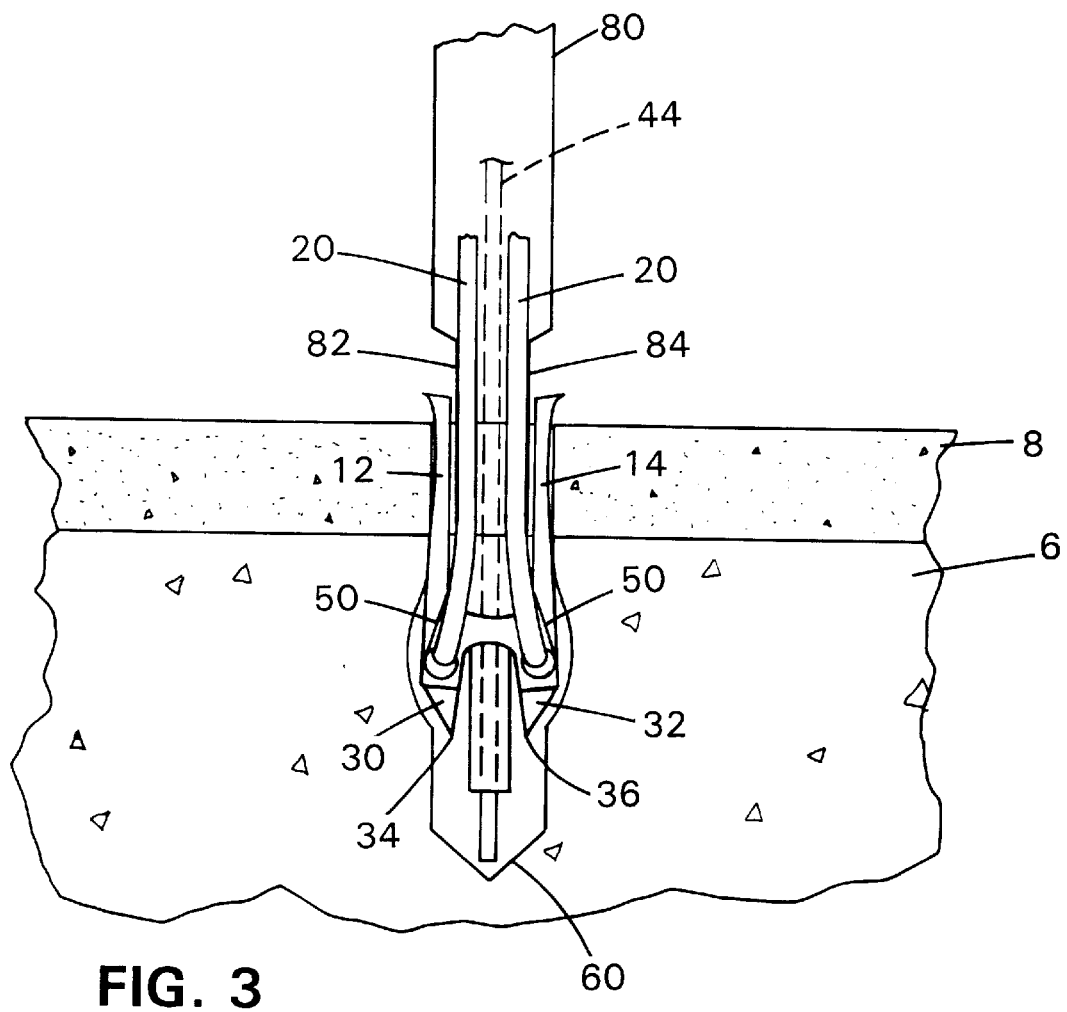
FIG. 3 shows the bone anchor of FIG. 1 during insertion into a bone hole.

Referring to FIGS. 2A–2C, legs 12, 14 include distal portions 30, 32, respectively, in the form of tapered cones separated by a slot 35 defined therebetween. Each distal portion 30, 32 terminates in a distal, bone penetrating end 34, 36. Proximal ends 16, 18 of legs 12, 14 are curved outwardly as shown in FIG. 2B. Distal portions 30, 32 are thicker than proximal portions 46, 48 of legs 12, 14. Legs 12, 14 are oriented parallel to each other and extend axially along a longitudinal axis 43. Legs 12, 14 are spaced from each other and joined by a transversely oriented bridge 40 located between proximal ends 16, 18 and distal ends 34, 36 of legs 12, 14. Bridge 40 has an axially extending hole 42 to allow passage of anchor 10 over a guidewire 44 (FIG. 3). Legs 12, 14 include flat inner surfaces 47, 49.

Legs 12, 14 each define a pair of axially extending grooves 50, 52 (FIG. 2C) adjacent to holes 22, 24 for receiving suture 20, which are passed through holes 22, 24 (located slightly distally of bridge 40). Grooves 50, 52 are dimensioned such that suture 20 resides entirely within the grooves; that is, the suture does not extend beyond diameter, D, of bridge 40.

Referring to FIG. 3, in use, with suture 20 placed through holes 22, 24, anchor 10 inserted over guidewire 44 through hole 42 into a pre-drilled bone hole 60. Alternatively, tips 34, 36 of anchor 10 enable anchor 10 to be driven into the bone directly, without pre-drilling bone hole 60. Since bone hole 60 generally cannot be directly visualized by the surgeon, placement of anchor 10 over a guidewire facilitates locating the bone hole during insertion of the anchor. An insertion tool 80, such as described in copending U.S. application Ser. No. 09/022,764, filed Feb. 12, 1998, titled BONE ANCHOR DELIVERY SYSTEM, supra, can be used to insert anchor 10 in bone hole 60. Insertion tool 80 includes flattened regions 82, 84 over which flat surfaces 47, 49 of legs 12, 14 are located during insertion of anchor 10 into bone hole 60.

As shown in FIG. 3, legs 12, 14 pivot about bridge 40 to elastically compress together when passing through cortical bone 8 in response to an insertion force. When anchor 10 is fully inserted into bone hole 60, with legs 12, 14 located within the softer cancellous bone 6, legs 12, 14 return to their initial, uncompressed state of FIG. 2A.

Referring again to FIG. 1, to deploy anchor 10 within bone hole 60, after removing guidewire 44, a withdrawal force is applied to anchor 10 by applying tension to suture 20 along arrows 62. With proximal ends 16, 18 of legs 12, 14 abutting the undersurface 8a of cortical bone 8, the applied tension acts to plastically deform legs 12, 14, causing proximal ends 16, 18 of the legs to splay outwardly away from longitudinal axis 43 and distal portions 30, 32 of the legs to pivot inwardly toward longitudinal axis 43.

Legs 12, 14 are fully deployed when distal ends 34, 36 of the legs are in contact, preventing further outward splaying of the proximal ends of the legs. To provide this limiting effect, distal portions 30, 32 have a length, 1, of, e.g., about 0.1 inch, and are spaced apart a distance, d, of, e.g., about 0.044 inch. By causing the proximal ends of the legs to plastically deform, the legs will remain in their splayed, anchoring positions after removal of the withdrawal force. The distal portions of the legs ensure that the legs cannot be deformed to such an extent that fracture of the anchor is possible.

Figure 4A:
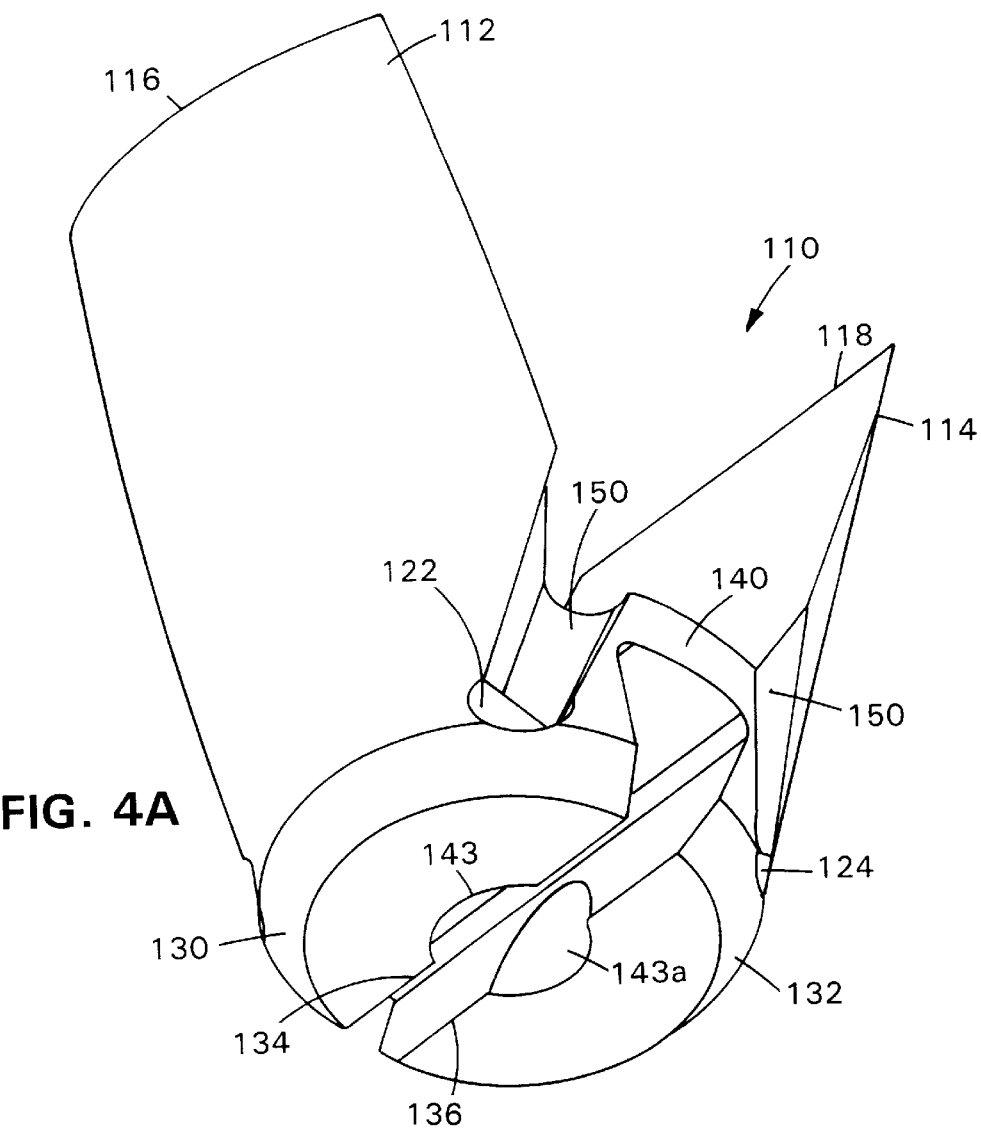
FIG. 4A is a perspective view of an alternative embodiment of a bone anchor.
Figure 4B:
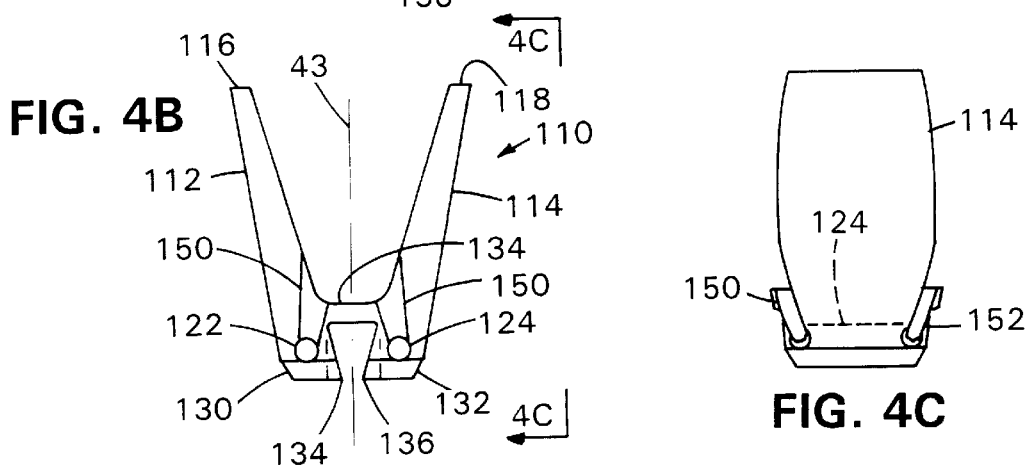
FIG. 4B is a side view of the bone anchor of FIG. 4A.
Figure 4C:
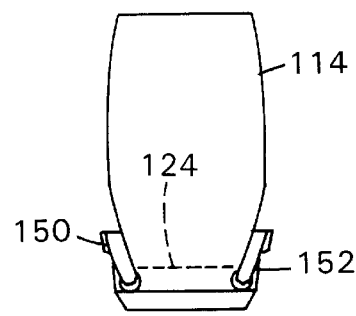
FIG. 4C is another side view of the bone anchor, taken along line 4C—4C of FIG. 4B.

Other embodiments are within the scope of the following claims. For example, referring to FIGS. 4A–4C, a suture anchor 110 for reattaching soft tissue 2 to bone 4 includes flexible anchoring legs 112, 114. Anchoring legs 112, 114 act to secure suture anchor 110 within cancellous bone 6, as described above with reference to FIGS. 1–3. Anchor 110 includes transverse holes 122, 124 for receiving a pair of sutures 20.

Legs 112, 114 include distal portions 130, 132, respectively. Legs 112, 114 are joined by a bridge 140 located between proximal ends 116, 118 and distal ends 134, 136 of legs 112, 114. Bridge 140 has an axially extending hole 142 oriented along longitudinal axis 43, and distal ends 130, 132 are chamfered at 143, 143a, respectively, to allow passage of anchor 110 over guidewire 44. Legs 112, 114 each define a pair of axially extending grooves 150, 152 (FIG. 4C) for receiving suture 20. As described above, grooves 150, 152 are dimensioned such that suture 20 resides entirely within the grooves.

In use, anchor 110 is inserted over guidewire 44 into pre-drilled bone hole 60. Legs 112, 114 elastically compress when passing through cortical bone 8. When anchor 110 is fully inserted into bone hole 60, with legs 112, 114 located within the softer cancellous bone 6, legs 112, 114 return to their initial, uncompressed state.

To deploy anchor 110 within bone hole 60, after removing guidewire 44, tension is applied to suture 20. With proximal ends 116, 118 of legs 112, 114 abutting the undersurface 8a of cortical bone 8, pulling proximally on suture 20 causing legs 112, 114 to pivot about bridge 140 plastically deforming legs 112, 114. Proximal ends 116, 118 of the legs splay outwardly and distal portions 130, 132 of the legs move inwardly toward each other. Legs 112, 114 are fully deployed when distal ends 134, 136 of the legs are in contact, preventing further splaying of the proximal ends of the legs.

Suture anchors 10 and 110 are preferably made from medical grade titanium, though other metals and polymers, including bioabsorble polymers can be used. Anchors 10 and 110 can be inserted into bone hole 60 without the use of a guidewire.

What is claimed is:

1. A bone anchor, comprising:
   a first anchoring leg having a proximal end and a distal end,
   a second anchoring leg having a proximal end and a distal end, and
   a bridge joining the first anchoring leg to the second anchoring leg intermediate the proximal and distal ends of the anchoring legs, the anchor having a longitudinal axis and a portion of each of the anchoring legs proximal of the bridge, in a non-deformed state, being oriented outwardly from the longitudinal axis.

2. The bone anchor of claim 1 wherein portions of the first and second anchoring legs on a proximal side of the bridge are configured to compress together in response to an insertion force applied to the bone anchor during insertion of the bone anchor into a bone hole.

3. The bone anchor of claim 2 wherein the portions of the first and second anchoring legs on the proximal side of the bridge are configured to undergo elastic deformation when compressed together.

4. The bone anchor of claim 1 wherein portions of the first and second anchoring legs on a proximal side of the bridge are configured to splay apart in response to a withdrawal force applied to the bone anchor when the bone anchor is located in a bone hole.

5. The bone anchor of claim 4 wherein the portions of the first and second anchoring legs on the proximal side of the bridge are configured to undergo plastic deformation when splayed apart.

6. The bone anchor of claim 4 wherein portions of the first and second anchoring legs on a distal side of the bridge are configured to compress together during application of the withdrawal force to limit splaying of the portions of the first and second anchoring legs on the proximal side of the bridge.

7. The bone anchor of claim 6 wherein the portions of the first and second anchoring legs on the distal side of the bridge define a slot therebetween, a width of the slot defining an amount of splaying of the first and second anchoring legs.

8. The bone anchor of claim 1 wherein the bridge is positioned transverse to the first and second anchoring legs.

9. The bone anchor of claim 1 wherein the bridge includes an opening oriented substantially parallel to the longitudinal axis for placement of the bone anchor over a guidewire.

10. The bone anchor of claim 1 further including a suture mount for attaching a suture to the bone anchor.

11. The bone anchor of claim 10 wherein the suture mount comprises a through hole in at least one of the first and second anchoring legs oriented transversely to the axis.

12. The bone anchor of claim 11 wherein the suture mount further includes an axially oriented groove located on an outer surface of the bone anchor, adjacent to and on either side of the through hole.

13. The bone anchor of claim 10 wherein the suture mount comprises a first transversely oriented through hole in the first anchoring leg and a second transversely oriented through hole in the second anchoring leg.

14. The bone anchor of claim 1 wherein said first and second anchoring legs each includes a distal end configured for penetrating bone tissue.

15. The bone anchor of claim 1 wherein said first and second anchoring legs each includes a flat inner surface for engaging a flattened region of an insertion tool.

16. The bone anchor of claim 1 wherein said first and second anchoring legs each includes an outwardly curved proximal end.

17. The bone anchor of claim 1 wherein the first and second anchoring legs other than at the outwardly oriented portion of the anchoring legs proximal of the bridge are oriented substantially parallel to each other.

18. The bone anchor of claim 1 wherein the bone anchor is formed from metal.

19. The bone anchor of claim 1 wherein the bone anchor is formed from a polymer.

20. A bone anchor, comprising:
a first anchoring leg having a proximal end and a distal end,
a second anchoring leg having a proximal end and a distal end, and
a bridge joining the first anchoring leg to the second anchoring leg intermediate the proximal and distal ends of the anchoring legs,
portions of the first and second anchoring legs on a proximal side of the bridge being configured to elastically compress together in response to an insertion force applied to the bone anchor, and to plastically splay apart in response to a withdrawal force applied to the anchor when the anchor is located in a bone hole, portions of the first and second anchoring legs on a distal side of the bridge being configured to plastically compress together during application of the withdrawal force to limit splaying of the portions of the first and second anchoring legs on the proximal side of the bridge.

21. The bone anchor of claim 20 wherein the bridge includes an axially oriented opening for placement of the bone anchor over a guidewire.

22. The bone anchor of claim 21 further including a transversely oriented opening for passage of a suture.

23. A bone anchor, comprising:
a plurality of anchoring legs each having a proximal end and a distal end,
proximal portions of the plurality of anchoring legs being configured to splay apart during application of a withdrawal force to the bone anchor when the bone anchor is located in a bone hole,
distal portions of the plurality of anchoring legs being configured to move together during application of the withdrawal force to limit splaying of the proximal portions of the plurality of anchoring legs.

24. A method for attaching soft tissue to bone, including inserting a bone anchor with attached suture into the bone, the bone anchor having a first anchoring leg, a second anchoring leg, and a bridge joining the first anchoring leg to the second anchoring leg intermediate proximal and distal ends of the anchoring legs, and
deploying the bone anchor within the bone by applying tension to the suture.

25. The method of claim 24 wherein the step of deploying includes pulling proximally on the suture to plastically splay apart proximal portions of the anchoring legs.

26. A bone anchor, comprising:
a first anchoring leg having a proximal end and a distal end,
a second anchoring leg having a proximal end and a distal end, and
a bridge joining the first anchoring leg to the second anchoring leg intermediate the proximal and distal ends of the anchoring legs, portions of the first and second anchoring legs on a proximal side of the bridge being configured to splay apart in response to a withdrawal force applied to the bone anchor when the bone anchor is located in a bone hole, the portions of the first and second anchoring legs on the proximal side of the bridge being configured to undergo plastic deformation when splayed apart.

27. A bone anchor, comprising:
a first anchoring leg having a proximal end and a distal end,
a second anchoring leg having a proximal end and a distal end, and
a bridge joining the first anchoring leg to the second anchoring leg intermediate the proximal and distal ends of the anchoring legs, portions of the first and second anchoring legs on a proximal side of the bridge are configured to splay apart in response to a withdrawal force applied to the bone anchor when the bone anchor is located in a bone hole, and portions of the first and second anchoring legs on a distal side of the bridge are configured to compress together during application of the withdrawal force to limit splaying of the portions of the first and second anchoring legs on the proximal side of the bridge.

28. The bone anchor of claim 27 wherein the portions of the first and second anchoring legs on the distal side of the bridge define a slot therebetween, a width of the slot defining an amount of splaying of the first and second anchoring legs.

29. A bone anchor, comprising:
a first anchoring leg having a proximal end and a distal end,
a second anchoring leg having a proximal end and a distal end, and
a bridge joining the first anchoring leg to the second anchoring leg intermediate the proximal and distal ends of the anchoring legs, wherein portions of the first and second anchoring legs on a proximal side of the bridge are configured to compress together in response to an insertion force applied to the bone anchor during insertion of the bone anchor into a bone hole.

30. The bone anchor of claim 29 wherein the portions of the first and second anchoring legs on the proximal side of the bridge are configured to undergo elastic deformation when so compressed together.

31. A bone anchor, comprising:
a first anchoring leg having a proximal end and a distal end, a second anchoring leg having a proximal end and a distal end, and a bridge joining the first anchoring leg to the second anchoring leg intermediate the proximal and distal ends of the anchoring legs, wherein portions of the first and second anchoring legs on a proximal side of the bridge are configured to splay apart in response to a withdrawal force applied to the bone anchor when the bone anchor is located in a bone hole.

32. A bone anchor, comprising:

a first anchoring leg having a proximal end and a distal end, a second anchoring leg having a proximal end and a distal end, and a bridge joining the first anchoring leg to the second anchoring leg intermediate the proximal and distal ends of the anchoring legs, wherein the bone anchor has a longitudinal axis and the bridge includes an opening oriented substantially parallel to the longitudinal axis for placement of the bone anchor over a guidewire.

33. A bone anchor, comprising:

a first anchoring leg having a proximal end and a distal end, a second anchoring leg having a proximal end and a distal end, a bridge joining the first anchoring leg to the second anchoring leg intermediate the proximal and distal ends of the anchoring legs, and a suture mount for attaching a suture to the bone anchor.

34. The bone anchor of claim 33 wherein the bone anchor has a longitudinal axis and the suture mount comprises a through hole in at least one of the first and second anchoring legs oriented transversely to the axis.

35. The bone anchor of claim 34 wherein the suture mount further includes an axially oriented groove located on an outer surface of the bone anchor, adjacent to and on either side of the through hole.

36. The bone anchor of claim 33 wherein the bone anchor has a longitudinal axis and the suture mount comprises a first through hole in the first anchoring leg oriented transversely to the axis, and a second through hole in the second anchoring leg oriented transversely to the axis.

* * * * *